(12) United States Patent
Roper et al.

(10) Patent No.: US 11,573,199 B2
(45) Date of Patent: Feb. 7, 2023

(54) DEVICES, SYSTEMS, AND METHODS FOR QUANTITATION OF INSULIN

(71) Applicant: The Florida State University Research Foundation, Inc., Tallahassee, FL (US)

(72) Inventors: Michael G. Roper, Tallahassee, FL (US); Rafael Arturo Masitas Castillo, Tallahassee, FL (US); Basel Bandak, Tallahassee, FL (US); Wesley James Eaton, Tallahassee, FL (US); Joel Elinam Alfred Adablah, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 282 days.

(21) Appl. No.: 16/862,014

(22) Filed: Apr. 29, 2020

(65) Prior Publication Data
US 2020/0340944 A1    Oct. 29, 2020

Related U.S. Application Data

(60) Provisional application No. 62/839,976, filed on Apr. 29, 2019.

(51) Int. Cl.
*G01N 27/447* (2006.01)
*B01L 3/00* (2006.01)
*G01N 33/74* (2006.01)

(52) U.S. Cl.
CPC .. *G01N 27/44791* (2013.01); *B01L 3/502715* (2013.01); *B01L 3/502792* (2013.01);
(Continued)

(58) Field of Classification Search
CPC ....... G01N 27/44791; G01N 27/44721; G01N 27/44773; G01N 33/74; G01N 33/54306;
(Continued)

(56) References Cited

U.S. PATENT DOCUMENTS

2002/0121444 A1    9/2002   Lee et al.
2004/0224002 A1   11/2004   Fishman
(Continued)

FOREIGN PATENT DOCUMENTS

AU           54220 01 A        10/2001

OTHER PUBLICATIONS

Zhang et al., "Advances in organ-on-a-chip engineering," Nature Reviews, vol. 3, Aug. 2018, pp. 257-278.
(Continued)

*Primary Examiner* — Jennifer Wecker
*Assistant Examiner* — Oyeleye Alexander Alabi
(74) *Attorney, Agent, or Firm* — Eversheds Sutherland (US) LLP

(57) ABSTRACT

Devices that may couple two or more apparatuses, such as an organ-on-a-chip device and a microfluidic device. Devices that include an organ-on-a-chip device, a microfluidic device, and a cap that couples the organ-on-a-chip device and the microfluidic device. Systems that include the devices and a detection unit. Methods for quantitation of insulin.

20 Claims, 5 Drawing Sheets

(52) U.S. Cl.
CPC . *G01N 27/44721* (2013.01); *G01N 27/44773* (2013.01); *G01N 33/74* (2013.01); *B01L 2200/10* (2013.01); *B01L 2300/042* (2013.01); *B01L 2300/06* (2013.01); *B01L 2300/0645* (2013.01); *B01L 2300/123* (2013.01); *B01L 2300/14* (2013.01)

(58) Field of Classification Search
CPC ........... G01N 33/5308; B01L 3/502715; B01L 3/502792; B01L 2200/10; B01L 2300/042; B01L 2300/06; B01L 2300/0645; B01L 2300/123; B01L 2300/14; B01L 2300/046; B01L 2400/0418
See application file for complete search history.

(56) References Cited

U.S. PATENT DOCUMENTS

| | | |
|---|---|---|
| 2008/0200343 A1 | 8/2008 | Clemens et al. |
| 2012/0083046 A1 | 4/2012 | Watson et al. |
| 2014/0356849 A1* | 12/2014 | Wikswo ................ B01L 3/5027 435/284.1 |
| 2018/0188230 A1* | 7/2018 | Huff ................. G01N 33/48721 |
| 2019/0071661 A1* | 3/2019 | Marshall ........... B01L 3/502776 |

OTHER PUBLICATIONS

Bandak et al., "Microfluidic-enabled quantitative measurements of insulin release dynamics from single islets of Langerhans in response to 5-palmitic acid hydroxy stearic acid," Lab Chip, vol. 18 (2018), pp. 2873-2882.

Schrel et al., "Online fluorescence anisotropy immunoassay for monitoring insulin secretion from islets of Langerhans," Anal. Methods, vol. 9 (2017), pp. 38-45.

Shang et al., "Emerging Droplet Microfluidics," Chemical Reviews vol. 117 (2017), pp. 7964-8040.

International Patent Application PCT/US2020/030461, International Search Report and Written Opinion, dated Jul. 23, 2020.

Temiz et al., "Lab-on-a-chip devices: How to close and plug the lab?" Microelectronic Engineering vol. 132 (2015), pp. 156-175.

* cited by examiner

DEVICES, SYSTEMS, AND METHODS FOR QUANTITATION OF INSULIN

CROSS-REFERENCE TO RELATED APPLICATIONS

This application claims priority to U.S. Provisional Patent Application No. 62/839,976, filed Apr. 29, 2019, which is incorporated herein by reference.

STATEMENT REGARDING FEDERALLY SPONSORED RESEARCH OR DEVELOPMENT

This invention was made with government support under contract no. 1UC4DK116283 awarded by the National Institutes of Health (NIH). The government has certain rights in this invention.

BACKGROUND

Diabetes is an increasing public health problem in the USA. The estimated number of people with diabetes in the USA is about 30 million, with an estimated total cost of healthcare associated with diagnosed diabetes of about $327 billion for 2017, according to the American Diabetes Association.

The loss of glucose homeostasis in the human body can result in two types of diabetes: type I and II. In these two types of diabetes, the focus of medical and basic research is concentrated on reestablishing functionality and/or replenishing islets of Langerhans in the patient under study or therapy.

In an effort to cure diabetes, researchers are using new drug treatments, islets transplantation from a cadaveric donor or β-cell cluster from in vitro differentiation of human pluripotent stem cells (hPSCs), or a combination thereof. The focus of these strategies is to increase insulin secretion to a level where glucose homeostasis is considered normal.

Due to the fact that insulin secretion by islet of Langerhans is a main indicator for evaluating the efficacy of a drug treatment, and a criteria for assessing the quality of islet for transplantation, researchers have used a glucose stimulated insulin secretion (GSIS) test as a method for measuring insulin secretion. In this test, islets of Langerhans are subjected to low and high glucose levels, and levels of insulin production are measured in both cases. The quantification of insulin is usually achieved by an enzyme-linked immunosorbent assay (ELISA) after the collection of several samples during a GSIS test. In this test, the sampling is manual or automatic, and the analysis is not in real time. Although ELISA systems are considered very sensitive and specific, this method is usually highly time-consuming, requires skilled analysts, and/or is expensive, with an estimated cost per GSIS test of about $600 for 40 data points (reagent cost).

To avoid the necessity of sampling by manual or automatic operations during GSIS tests, some researches have used electrophoretic immunoassay methods, and a microfluidic device approach to quantify insulin from one or more islets of Langerhans. This approach has been applied during the last decade for the study of how the secretion and coupling of islets of Langerhans contribute to proper glucose clearance in the body. The electrophoretic immunoassay method is well stablished, but its use is not widespread as a standard methodology, typically due to the dimensions of the instrument and/or the absence of expertise in the application of the method by other groups.

There remains a need for methods, devices, and systems that allow for the quantitation of insulin in real time, are relatively inexpensive, or a combination thereof.

BRIEF SUMMARY

Provided herein are embodiments of methods, devices, and systems, such as compact instruments, for the quantitation of insulin. The quantitation of insulin may be achieved in at least near real time using embodiments of the methods, devices, and systems herein. The devices, systems, and methods described herein may permit the quantitation of insulin at a fraction of the cost of a traditional ELISA method.

In some embodiments, the devices, systems, and methods achieve the quantitation of insulin via an immunoassay method with a device that provides an interface between an organ-on-a-chip device and a microfluidic device.

In one aspect, devices are provided. In some embodiments, the devices are configured to provide an interface between two apparatuses. The devices may include a cap for a reservoir, wherein the cap defines a first opening and a second opening, a capillary tube arranged in the first opening of the cap, and an electrode arranged in the second opening of the cap. In some embodiments, the devices also include a reservoir. The reservoir may have a first surface at a first end of the reservoir, and a second surface at a second end of the reservoir, wherein the first surface defines a first void, and the second surface defines a second void, and the cap is arranged at the first end of the reservoir, and overlays or plugs the first void of the reservoir.

In some embodiments, the devices include a microfluidic device. The microfluidic device may include (i) a first orifice defined by a first surface of the microfluidic device, (ii) a second orifice defined by the first surface of the microfluidic device, (iii) a third orifice defined by a second surface of the microfluidic device, (iv) a main channel defined by one or more first internal surfaces of the microfluidic device, wherein the first orifice and the second orifice are in fluid communication with each other via the main channel, and (v) an electroosmotic flow channel defined by one or more second internal surfaces of the microfluidic device, wherein the main channel is in fluid communication with the third orifice via the electroosmotic flow channel. The reservoir may be arranged on the first surface of the microfluidic device at a position at which the second void of the reservoir at least partially aligns with the first orifice of the microfluidic device.

In some embodiments, the devices include an organ-on-a-chip device. The organ-on-a-chip device may include a channel outlet, and a capillary tube has a second end that is at least partially inserted into the channel outlet.

In another aspect, systems are provided herein. In some embodiments, the systems include a device as described herein, and a detection unit. The detection unit may include an optical system unit, a laser unit, an ampere meter, a temperature meter, a gate unit, a high-voltage unit, or a combination thereof. The systems may include a housing in which a device, a detection unit, or a device and a detection unit are disposed.

In another aspect, methods of quantitating insulin are provided. In some embodiments, the methods include (i) providing a system as described herein, wherein the organ-on-a-chip comprises a sample, and (ii) quantitating an amount of insulin secreted from the sample. The quantitating of the amount of insulin may include performing an electrophoretic immunoassay or a fluorescence anisotropy immunoassay.

Additional aspects will be set forth in part in the description which follows, and in part will be obvious from the description, or may be learned by practice of the aspects described herein. The advantages described herein will be realized and attained by means of the elements and combinations particularly pointed out in the appended claims. It is to be understood that both the foregoing general description and the following detailed description are exemplary and explanatory only and are not restrictive.

DETAILED DESCRIPTION

Devices, systems, and methods are provided herein, which may be used in a number of methods, including methods for the quantitation of insulin.

Devices

In one aspect, devices are provided that are configured to provide an interface between two apparatuses, such as an organ-on-a-chip device and a microfluidic device. Other apparatuses, however, may be used with the devices provided herein.

In some embodiments, the devices include (i) a cap for a reservoir, wherein the cap defines a first opening and a second opening, (ii) a capillary tube arranged in the first opening of the cap, and (iii) an electrode arranged in the second opening of the cap. A cap may be formed of any material that does not undesirably impact the methods performed with the devices.

A capillary tube and/or electrode "arranged" in the first or second opening may be fixably mounted or slidably mounted in the first opening and second opening, respectively. A material, such as an insulating material, adhesive, etc., may be arranged between a cap and at least one of a capillary tube and electrode.

Figure 1A:
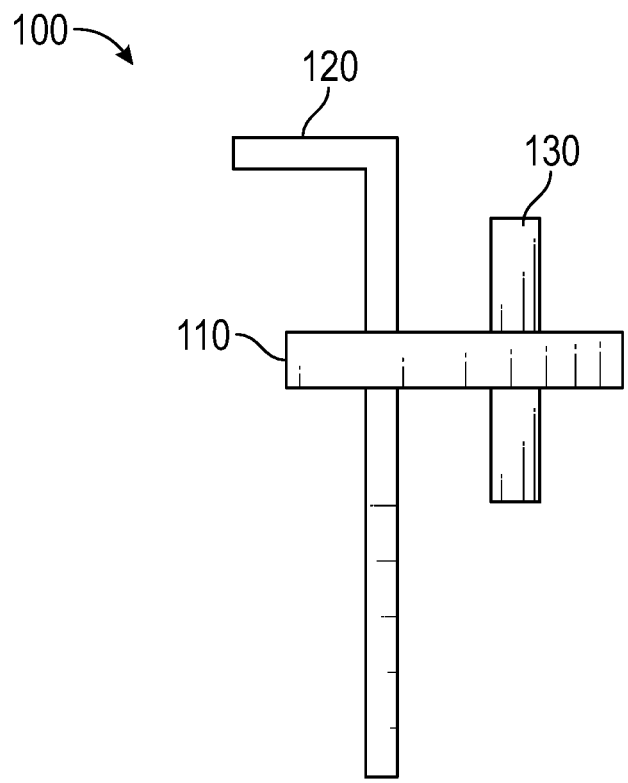
FIG. 1A depicts a schematic (side view) of an embodiment of a device described herein.
Figure 1B:
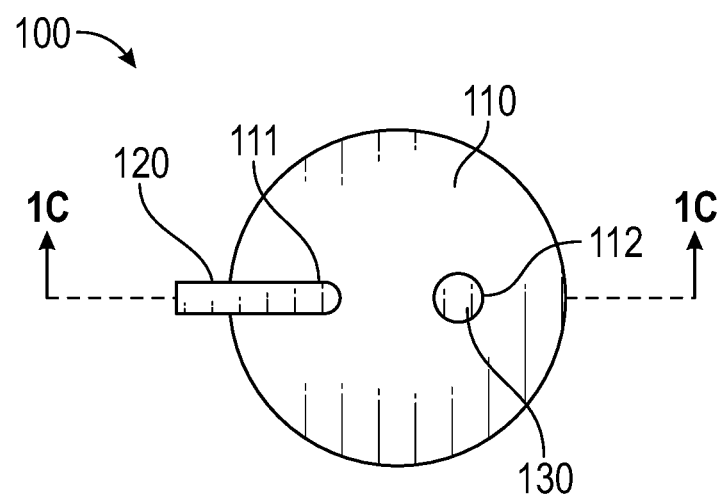
FIG. 1B depicts a plan view of the embodiment of the device depicted at FIG. 1A.
Figure 1C:
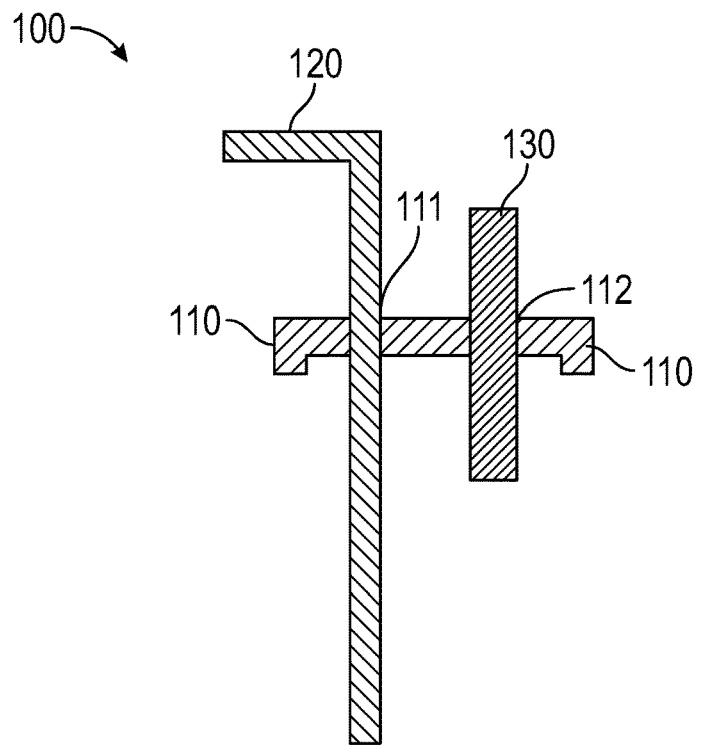
FIG. 1C depicts a cross-sectional view of the embodiment of the device depicted at FIG. 1A and FIG. 1B.

An embodiment of a device is depicted schematically at FIG. 1A (side view), FIG. 1B (plan view), and FIG. 1C (cross-sectional view). The device 100 includes a cap 110 for a reservoir. The cap 110 defines a first opening 111 and a second opening 112. A capillary tube 120 is arranged in the first opening 111, and an electrode 130 is arranged in the second opening 112.

Any electrode may be included in the devices provided herein. In some embodiments, the electrode is a platinum electrode.

A capillary tube of any size may be included in the devices provided herein. In some embodiments, a capillary tube has an internal diameter of about 80 µm to about 120 µm, and an outer diameter of about 140 µm to about 180 µm. In some embodiments, a capillary tube has an internal diameter of about 90 µm to about 110 µm, and an outer diameter of about 150 µm to about 170 µm. A capillary may have any length. The length, in some embodiments, is sufficient to position one terminus of the capillary tube in a main channel of a microfluidic device, and the other terminus of the capillary tube in an organ-on-a-chip device.

A cap may be formed of any material that does not undesirably impact the methods performed with the devices. A cap also may have any size that is effective to accommodate a capillary tube and an electrode. In some embodiments, the cap has an outer diameter or outer largest dimension of about 1 mm to about 20 mm, about 1 mm to about 15 mm, or about 2 mm to about 12 mm, or about 8 mm to about 12 mm.

In some embodiments, the devices also include a reservoir. In some embodiments, the reservoir has a first surface at a first end of the reservoir, and a second surface at a second end of the reservoir. The first surface may define a first void, and the second surface may define a second void, and the cap may be arranged at the first end of the reservoir.

In some embodiments, a reservoir has an inner diameter or inner largest dimension of about 330 µm to about 400 µm, about 330 µm to about 380 µm, or about 330 µm to about 350 µm. The first void may have a diameter or inner largest dimension that is equal to or less than the inner diameter or inner largest dimension of the reservoir.

The cap may overlay or plug the first void of the reservoir. A cap, for example, may have a shape and a surface area that permits the cap to overlay, i.e., cover, a first void of a reservoir entirely. The cap, therefore, may contact all or a portion of a first surface of a reservoir. A cap, as a further example, may have a shape and a surface area that permits the cap to plug, i.e., be inserted at least partially into, a first void of a reservoir. If a first void has a diameter or largest dimension of about 330 µm, then a cap may have a diameter or largest dimension equal to or greater than 330 µm.

In some embodiments, the devices include a microfluidic device. The microfluidic devices may include a first orifice defined by a first surface of the microfluidic device, a second orifice defined by the first surface of the microfluidic device, a third orifice defined by a second surface of the microfluidic device, a main channel defined by one or more first internal surfaces of the microfluidic device, wherein the first orifice and the second orifice are in fluid communication with each other via the main channel, and an electroosmotic flow channel defined by one or more second internal surfaces of the microfluidic device, wherein the main channel is in fluid communication with the third orifice via the electroosmotic flow channel.

The terms "opening", "void", and "orifice", as used herein, have the same meaning and are interchangeable, but, in the interest of clarity, these terms are used to describe features of the caps, reservoirs, and microfluidic devices, respectively.

The first orifice of a microfluidic device may have any dimensions sufficient to accommodate a capillary tube, an electrode, or a capillary tube and an electrode. In some embodiments, the first orifice has a diameter or largest dimension of about 280 µm to about 320 µm, about 290 µm to about 310 µm, or about 300 µm. The second orifice may have any dimensions, including dimensions that are sufficient to permit a pressure of a gas to maintain a flow of a perfusate between the capillary tube and the microfluidic device. In some embodiments, the pressure is atmospheric pressure, the gas is air, or a combination thereof. The third orifice may have any dimensions. The third orifice may have a diameter or largest dimension equal to or different than the inner diameter or inner largest dimension of an electroosmotic flow channel.

The reservoir described herein may be arranged on the first surface of a microfluidic device at a position at which the second void of the reservoir at least partially aligns with the first orifice of the microfluidic device. In some embodiments, a second void of a reservoir and a first orifice of a microfluidic device align to an extent effective to accommodate a capillary tube that traverses both the second void and the first orifice. A reservoir arranged on a microfluidic device may be fixably or detachably mounted to the microfluidic device.

A cap, as described herein, may be arranged at a first end of the reservoir. In some embodiments, a capillary tube has a first end having a first terminus, and the first terminus is positioned in the main channel of the microfluidic device. In some embodiments, the first terminus of the capillary tube is positioned below an interface of the main channel and the electroosmotic flow channel when the device, the reservoir, and the microfluidic device are at an upright position. In some embodiments, the electrode has a first terminus that is positioned in the reservoir.

Figure 2A:
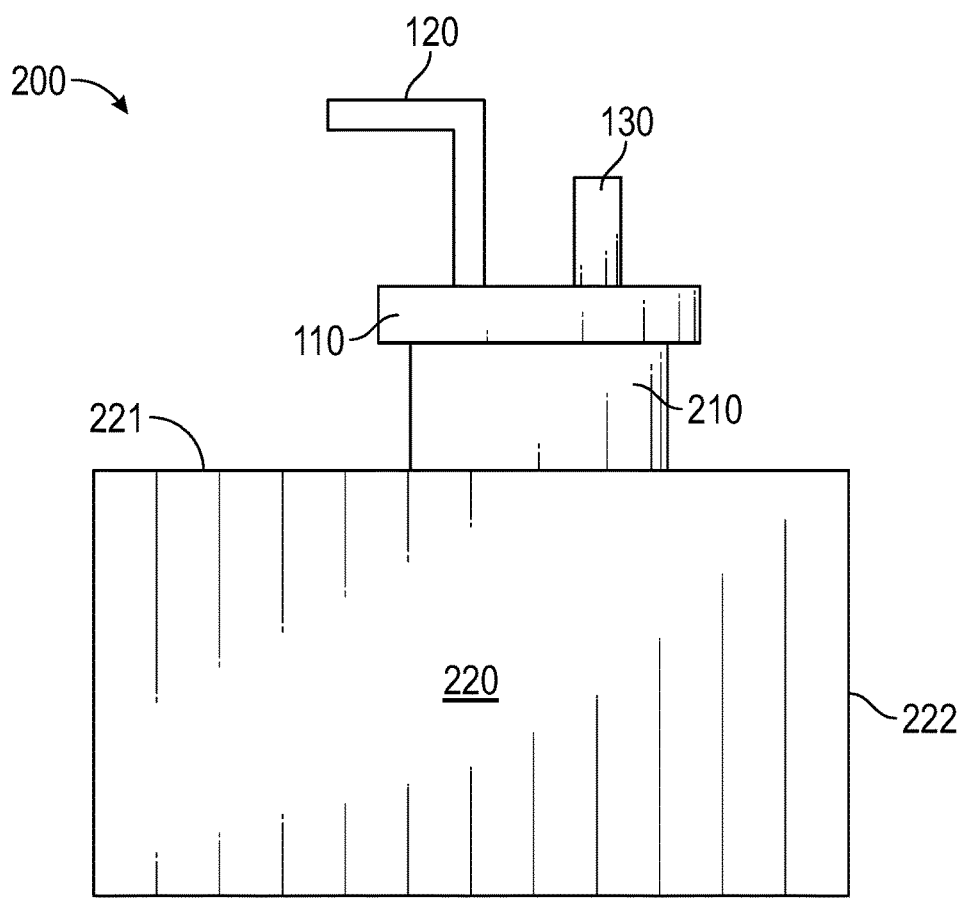
FIG. 2A depicts a schematic (side view) of an embodiment of a device described herein.
Figure 2B:
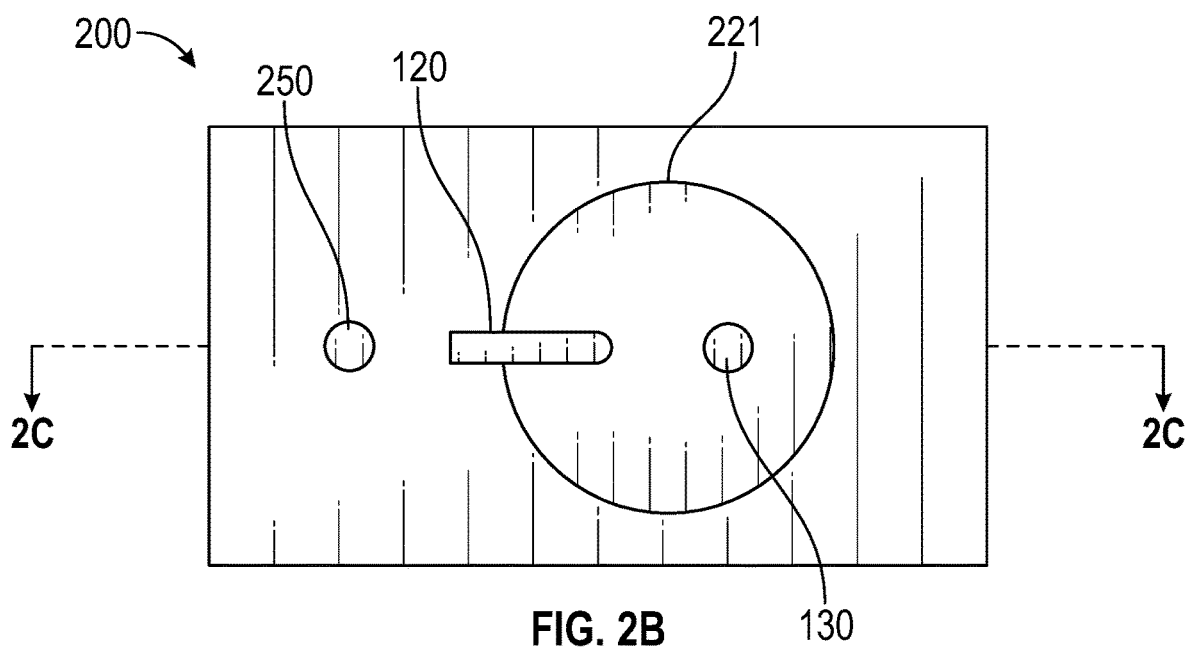
FIG. 2B depicts a plan view of the embodiment of the device depicted at FIG. 2A.
Figure 2C:
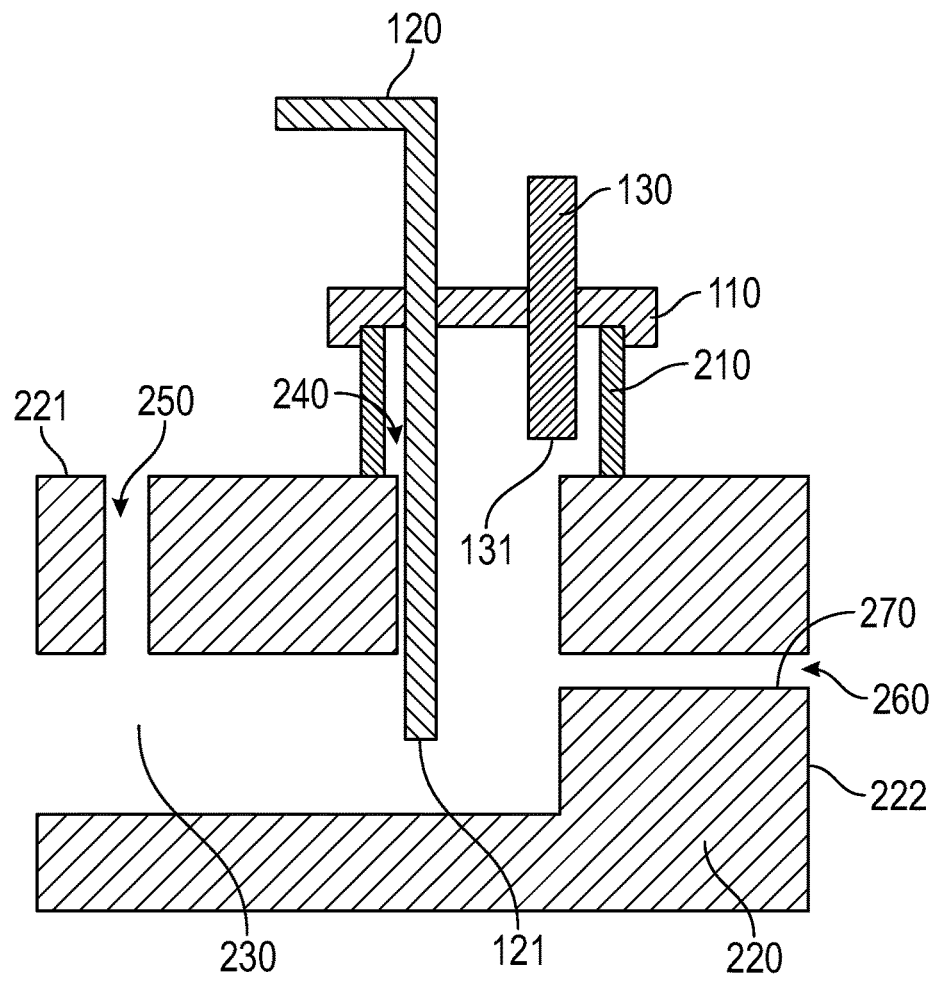
FIG. 2C depicts a cross-sectional view of the embodiment of the device depicted at FIG. 2A and FIG. 2B.

An embodiment of a device is depicted schematically at FIG. 2A (side view), FIG. 2B (plan view), and FIG. 2C (cross-sectional view). The device 200 includes a reservoir 210 arranged on a microfluidic device 220. The microfluidic device has a first surface 221 that defines a first orifice 240 and a second orifice 250. The microfluidic device 220 has a second surface 222 that defines a third orifice 260. The first orifice 240 and the second orifice 250 are in fluid communication with each other via a main channel 230. The main channel 230 is in fluid communication with the third orifice 260 via an electroosmostic flow channel 270. The cap 100 of FIGS. 1A-C is arranged at a first end of the reservoir 210. The capillary tube 120 has a first terminus 121 that is positioned in the main channel 230 at a location below the interface of the main channel 230 and the electroosmotic flow channel 270. The electrode 130 has a first terminus 131 that is positioned in the reservoir 210.

In some embodiments, the devices provided herein include an organ-on-a-chip device. The organ-on-a-chip device may include a channel outlet, and a capillary tube of a cap may have a second end that is at least partially inserted into the channel outlet. The channel outlet is formed at least in part of an elastic material.

Any organ-on-a-chip device may be used in the devices, systems, and methods provided herein. The organ-on-a-chip device typically is a microfluidic platform that may mimic the functionality of a living organ. Non-limiting examples of types of organ-on-a-chip devices include liver, heart, lung, gut, and others. In some embodiments, the caps described herein couple an organ-on-a-chip device with an electrophoretic immunoassay device for the quantitation of a material, such as insulin, protein(s), hormone(s), etc., released from islet of Langerhans.

When the devices provided herein include an organ-on-a-chip device, a flow of perfusate may be a flow to and/or from the organ-on-chip device from and/or to, respectively, a microfluidic device. The flow of perfusate may be continuous.

Figure 3:
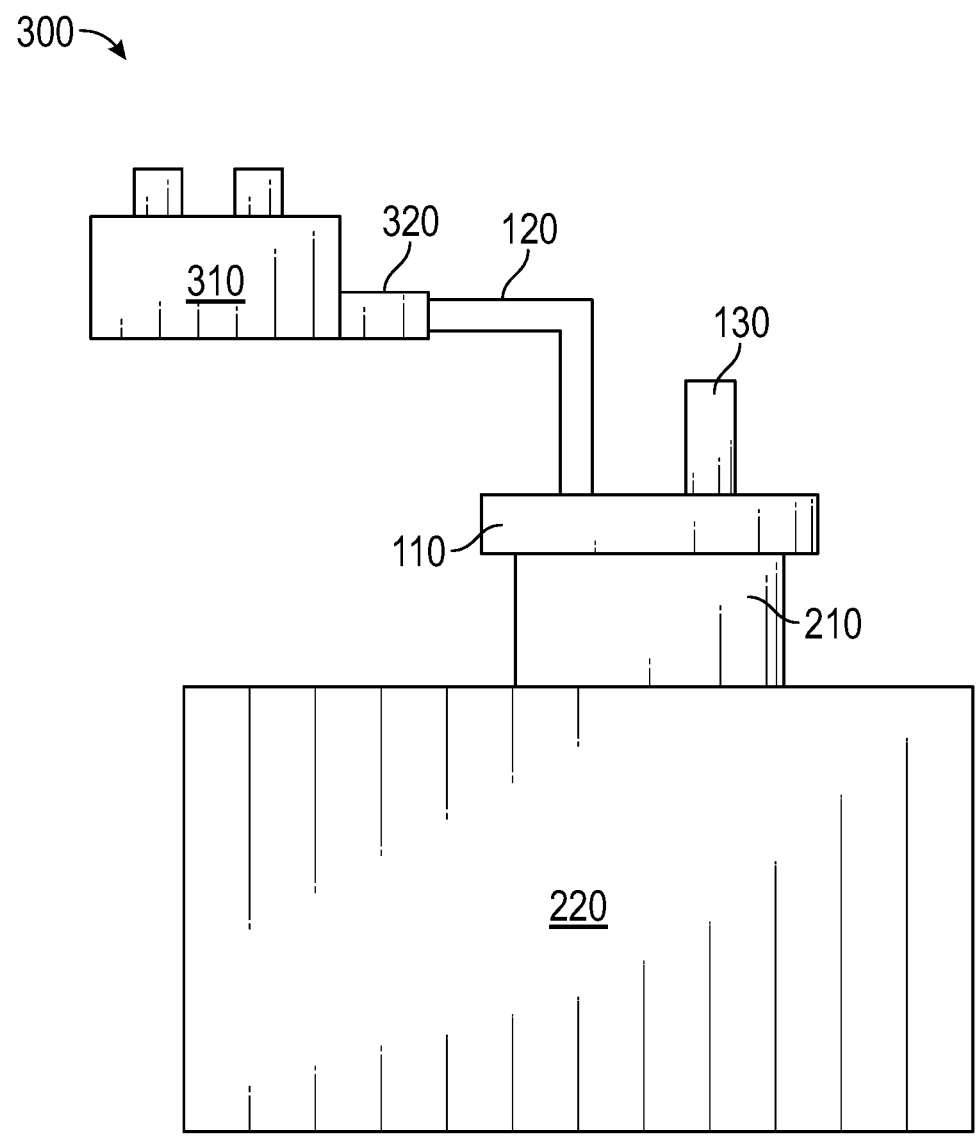
FIG. 3 depicts an embodiment of a device described herein.

An embodiment of a device is depicted schematically at FIG. 3. The device 300 includes the cap 110 of FIGS. 1A-1C arranged at the first end of the reservoir 210, which is arranged on the microfluidic device 220 of FIGS. 2A-2C. The capillary tube 120 of the cap 110 has a second end that is arranged in a channel outlet 320 of an organ-on-a-chip 310 device.

Systems

In another aspect, systems are provided herein. In some embodiments, the systems include a device as described herein, and a detection unit. The detection may include an optical system unit, a laser unit, an ampere meter, a temperature meter, a gate unit, a high-voltage unit, or a combination thereof.

In some embodiments, the systems include a housing. A device, a detection unit, or a device and a detection unit may be disposed in a housing. The dimensions of a housing may not exceed 50 cm×40 cm×40 cm.

Figure 4:
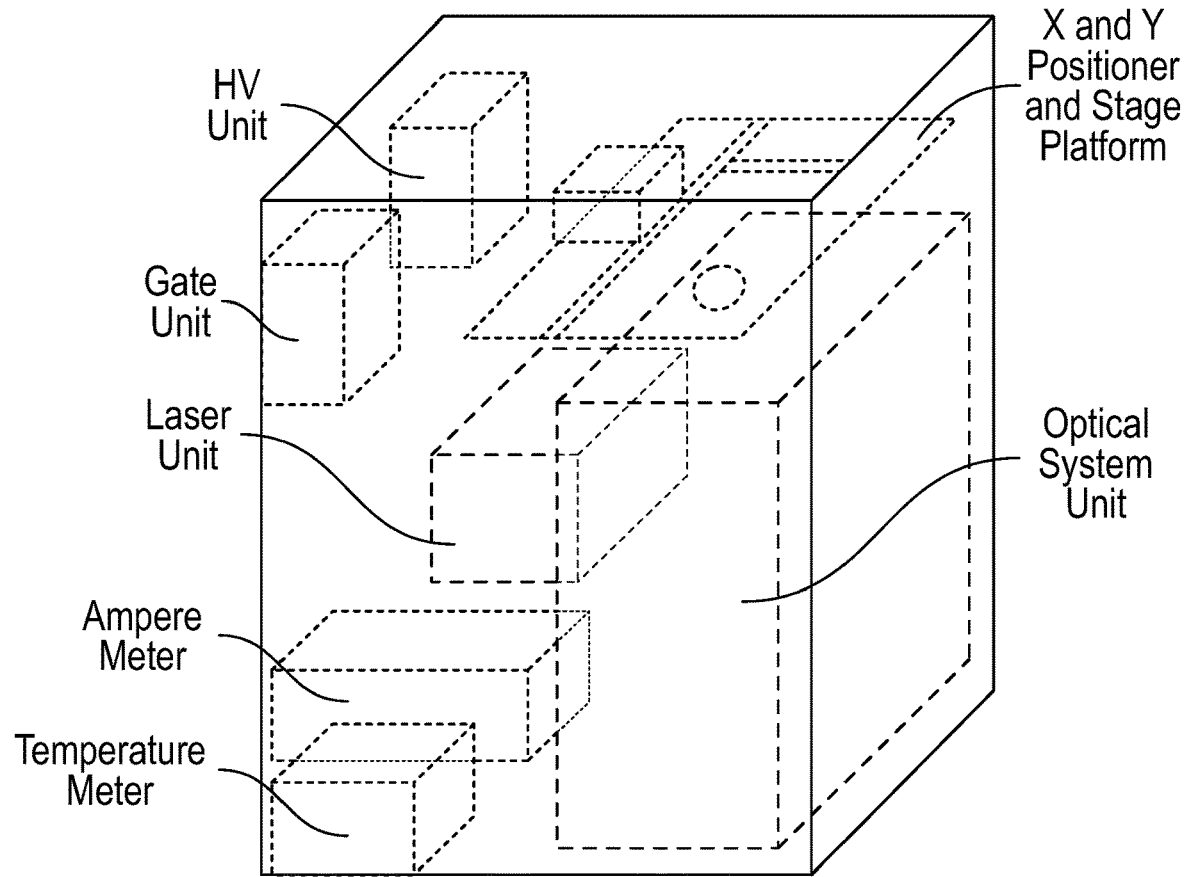
FIG. 4 depicts an embodiment of a system described herein.

An embodiment of a system is depicted at FIG. 4, and described at Example 3.

Figure 5:
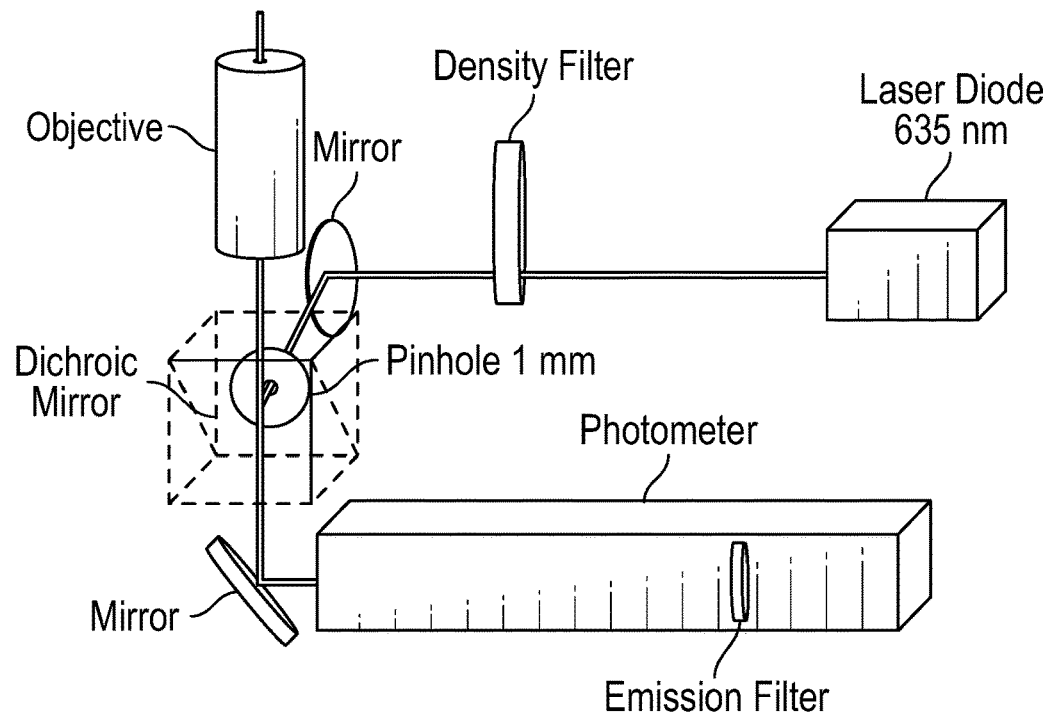
FIG. 5 depicts an embodiment of an optical system unit that may be included in the systems provided herein.

An embodiment of a laser unit and optical system unit is depicted herein at Example 1. An embodiment of a laser unit and an optical system unit are depicted at FIG. 5. The optical system unit may include a density filter, a mirror, a dichroic mirror, a photometer, or a combination thereof.

Methods

Methods also are provided herein, including methods of quantitating insulin. In some embodiments, the methods include (i) providing a system as described herein, wherein the organ-on-a-chip device comprises a sample, and (ii) quantitating an amount of insulin secreted from the sample. In some embodiments, the methods include providing a system as described herein, disposing a sample on or in the organ-on-a-chip device, and quantitating an amount of insulin secreted from the sample.

In some embodiments, the sample includes islets of Langerhans.

The quantitating of the amount of insulin may include performing any test, such as an electrophoretic immunoassay or a fluorescence anisotropy immunoassay. Embodiments of the devices described herein can be used in other electrophoretic immunoassay methods. For example, embodiments of the instruments described herein may be used to achieve the quantification of other peptides released from islets of Langerhans.

In some embodiments, a perfusate flows continuously from the organ-on-a-chip to the detection unit during the quantitating of the amount of insulin.

The devices, systems, and methods described herein may be used to quantitate materials other than insulin, such as proteins, hormones, etc., that may be secreted by a sample. An organ-on-chip device used in the systems described herein may host one or more stem cells.

While certain aspects of conventional technologies have been discussed to facilitate disclosure of various embodiments, applicants in no way disclaim these technical aspects, and it is contemplated that the present disclosure may encompass one or more of the conventional technical aspects discussed herein.

The present disclosure may address one or more of the problems and deficiencies of known methods and processes. However, it is contemplated that various embodiments may prove useful in addressing other problems and deficiencies in a number of technical areas. Therefore, the present disclosure should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

In the descriptions provided herein, the terms "includes," "is," "containing," "having," and "comprises" are used in an open-ended fashion, and thus should be interpreted to mean "including, but not limited to." When devices, methods, or systems are claimed or described in terms of "comprising" various steps or components, the devices, methods, or systems can also "consist essentially of" or "consist of" the various steps or components, unless stated otherwise.

The terms "a," "an," and "the" are intended to include plural alternatives, e.g., at least one. For instance, the disclosure of "a capillary tube," "an electrode," "a microfluidic device", and the like, is meant to encompass one, or mixtures or combinations of more than one capillary tube, electrode, microfluidic device, and the like, unless otherwise specified.

Various numerical ranges may be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicant discloses, in some embodiments, that the cap has an outer diameter or outer largest dimension of about 2 mm to about 12 mm. This range should be interpreted as encompassing about 2 mm and about 12 mm, and further encompasses "about" each of 3 mm, 4 mm, 5 mm, 6 mm, 7 mm, 8 mm, 9 mm, 10 mm, or 11 mm, including any ranges and sub-ranges between any of these values.

As used herein, the term "about" means plus or minus 10% of the numerical value of the number with which it is being used.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1—Laser-Induced Detection Immunoassay

A laser diode (635 nm) with a power of 100 mW was used as an exciting light source. The light was passed through a density filter wheel, and a pinhole mounted in front of a dichroic filter cube that contained a 650/750 nm dichroic mirror.

The light was redirected to an objective of 40×, 0.6 numerical aperture (NA)(Nikon Instruments, Inc.), and the emission collected through the same objective and in the direction of the dichroic mirror, spatial filter, 630/650 nm notch filter (Omega), and photomultiplier tube (PMT)(Hamamatsu Photonics, Middlesex, N.J.). A photometer (Photon Technology International, Inc., Birmingham, N.J.) housed the spatial filter, notch filter, and PMT. The LIF (logical interface) data acquisition was made possible through the use of a program written in LABVIEW® software (National Instruments, Austin, Tex.).

Example 2—Insulin Immunoassay Protocol

Microfluidic devices were conditioned for 30 minutes with 1 M NaOH, deionized water, and immunoassay reagents before each experiment. For all experiments, 150 nM Cy5-labeled insulin (Ins*) and 150 nM monoclonal anti-insulin (Ab) were used in the devices, and were prepared daily in a buffer containing 25 mM tricine, 1 mM ethylenediaminetetraacetic acid (EDTA), and 40 mM NaCl at pH 7.4, supplemented with 1 mg mL$^{-1}$ bovine serum albumin (BSA) and 0.1% TWEEN® 20 detergent (Sigma-Aldrich, USA).

Gate and waste reservoirs contained 150 mM tricine and 20 mM NaCl with p-adjusted to 7.4. During the experiments, the Ins*, Ab, and capillary reservoirs were grounded and −5000 V was applied to the waste reservoir with a high voltage power supply (UltraVolt, Inc., South Thief River Falls, Minn.). A flow-gated injection scheme was used to inject a sample into the separation channel using a high voltage relay (GIGAVAC, Carpinteria, Calif.).

For calibration curves, 0-1500 nM insulin prepared in balanced salt solution was perfused into the islet reservoir and the ratio of bound (B) and free (F) Ins* (B/F) was monitored. The concentrations of immunoassay reagents were referred to as the concentration in the fully mixed state, which assumed a 3-fold dilution of the concentrations in the microfluidic reservoirs.

Example 3—Interface Organ-On-A-Chip LIF Compact Instrument

The interface between an organ-on-a-chip and an electrophoretic microfluidic device was made possible in this example by the design and construction of an interface device, i.e., an embodiment of a cap described herein. The interface device of this example had two characteristics, which allowed (i) the continuous flow of perfusate from the organ-on-a-chip device to the electrophoretic microfluidic chip device by hydrostatic pressure driving force, (ii) an electrophoretic sampling of perfusate at the end of the capillary tube.

The incorporation of a platinum electrode in the design of the interface device permitted an electric continuity, from the reservoir where the capillary tube was located to the separation channel located at the same microfluidic device.

The device of this example had the structure depicted schematically at FIGS. 1A-1C, 2A-2C, and 3.

In this example, a cap was placed over a reservoir previously bonded to an electrophoretic microfluidic device. The orientation of the capillary tube and Pt electrode in the interface device made it possible to (i) bring perfusate from the organ-on-a-chip, and (ii) conduct sampling at the entrance of the electroosmotic flow (EOF) channel located in the electrophoretic microfluidic device. Also, an additional access hole, i.e., second orifice, was located in the electrophoretic microfluidic device to permit the introduction of atmospheric pressure, which kept a continuous flow of perfusate, thereby avoiding the saturation of the medium with insulin during a glucose-stimulated insulin secretion (GSIS) test.

To make the connection between the organ-on-a-chip and the interface device, i.e., cap, the capillary tube was inserted directly into the organ-on-a-chip device.

A 100 µm internal diameter (I.D.)/167 µm outer diameter (O.D.) capillary tube (Polymicro Technologies), was inserted into a 100 µm diameter channel outlet of the organ-on-a-chip device made of polydimethylsiloxane (PDMS). To keep a tight connection, the insertion placed approximately 0.4 cm of the capillary tube into the PDMS channel of the organ-on-a-chip.

The flexibility of the PDMS allowed the insertion of the capillary into the PDMS device in a direct way. In the instrument, i.e., system, used in this example, the components (when at an upright position) were spatially arranged so that the organ-on-a-chip device was above the microfluidic device, which, in turn, was above the optical system unit.

The organ-on-a-chip was placed in an elevated stand to allow the continuous flow of perfusate to the electrophoretic microfluidic chip device of this example. The electrophoretic microfluidic chip device was located above the optical system to bring the laser light to the separation channel located in the microfluidic device.

The compact system of this example was built by using an embodiment of the caps described herein to provide a new interface between the organ-on-a-chip and the glass electrophoretic chip. This combination permitted an almost real time analysis of insulin from an organ-on-chip device.

A schematic of the instrument used in this example is depicted at FIG. 4. The instrument included a housing having dimensions of 46 cm×32 cm×40 cm, and in the housing were arranged an X and Y positioner and stage platform, high-voltage unit (HV unit), gate unit, laser unit, optical system unit, ampere meter, and temperature meter.

The system of this example included an optical system unit. The optical system unit of this example included the components and spatial arrangement depicted at FIG. 5. FIG. 5 depicts the arrangement of the optical components located inside the embodiment of the optical system unit used in this example.

Islets loaded in the microfluidic organ-on-a-chip device were interfaced with the "detection" device. The interface between the two devices was accomplished using a capillary tube of 100 µm inner diameter (I.D.) that permitted a continuous flow of perfusate from the organ-on-a-chip to the detection chip. The instrument measured the insulin in the perfusate in one of two ways, both relying on antibody-based assays.

For rapid analysis, the system used a fluorescence anisotropy immunoassay for quantitation of insulin; for higher sensitivity measurements, an electrophoretic immunoassay was used. In contrast to traditional methods of quantification of insulin, such as ELISA, these configurations allowed near real time quantification of insulin at low cost. Due to the instrument's compact design and straight-forward use, it was suitable for many research laboratories that wish to examine insulin release from islets of Langerhans.

The arrangement of optical and electrical components of the systems of the examples herein allowed for a compact design that facilitated the portability of the instrument.

We claim:

1. A device for use in quantitation of insulin, the device comprising:
   a cap for a reservoir, wherein the cap defines a first opening and a second opening, wherein said first opening and said second opening are disposed at distinct locations of the cap;
   a capillary tube disposed in the first opening of the cap; and
   an electrode disposed in the second opening of the cap, wherein the electrode has a first terminus that is positioned in the reservoir,
   wherein the device is configured to provide an interface between an organ-on-a-chip device and a microfluidic device.

2. The device of claim 1, wherein the electrode comprises platinum.

3. The device of claim 1, wherein the capillary tube has an internal diameter of about 80 µm to about 120 µm, and an outer diameter of about 140 µm to about 180 µm.

4. The device of claim 1, further comprising the reservoir, wherein:
   the reservoir has a first surface at a first end of the reservoir, and a second surface at a second end of the reservoir;
   the first surface defines a first void, and the second surface defines a second void; and
   the cap is arranged at the first end of the reservoir, and overlays or plugs the first void of the reservoir.

5. The device of claim 4, wherein the reservoir has an inner diameter or inner largest dimension of about 330 µm to about 400 µm.

6. The device of claim 4, further comprising the microfluidic device, wherein the microfluidic device comprises:
   a first orifice defined by a first surface of the microfluidic device,
   a second orifice defined by the first surface of the microfluidic device,
   a third orifice defined by a second surface of the microfluidic device,
   a main channel defined by one or more first internal surfaces of the microfluidic device, wherein the first orifice and the second orifice are in fluid communication with each other via the main channel, and
   an electroosmotic flow channel defined by one or more second internal surfaces of the microfluidic device, wherein the main channel is in fluid communication with the third orifice via the electroosmotic flow channel; and
   wherein the reservoir is arranged on the first surface of the microfluidic device at a position at which the second void of the reservoir at least partially aligns with the first orifice of the microfluidic device.

7. The device of claim 6, wherein the first orifice has a diameter or a largest dimension of about 280 µm to about 320 µm.

8. The device of claim 6, wherein the capillary tube has a first end having a first terminus, and the first terminus is positioned in the main channel of the microfluidic device.

9. The device of claim 8, wherein the first terminus of the capillary tube is positioned below an interface of the main channel and the electroosmotic flow channel when the device, the reservoir, and the microfluidic device are at an upright position.

10. The device of claim 6, wherein the second orifice is configured to permit a pressure of a gas to maintain a flow of a perfusate between the capillary tube and the microfluidic device.

11. The device claim 10, wherein (i) the pressure is atmospheric pressure, (ii) the gas is air, or (iii) a combination thereof.

12. The device of claim 1, further comprising the organ-on-a-chip device, wherein the organ-on-a-chip device comprises a channel outlet, and the capillary tube has a second end that is at least partially inserted into the channel outlet.

13. The device of claim 12, wherein the channel outlet is formed at least in part of an elastic material.

14. A system comprising:
the device of claim 13, and a detection unit comprising an optical system unit, a laser unit, an ampere meter, a temperature meter, a gate unit, or a combination thereof.

15. The system of claim 14, further comprising a housing in which the device, the detection unit, or the device and the detection unit are disposed.

16. A method of quantitating insulin, the method comprising:
providing the system of claim 15, wherein the organ-on-a-chip device comprises a sample; and
quantitating an amount of insulin secreted from the sample.

17. The method of claim 16, wherein the sample comprises islets of Langerhans.

18. The method of claim 16, wherein the quantitating of the amount of insulin comprises performing an electrophoretic immunoassay or a fluorescence anisotropy immunoassay.

19. The method of claim 16, wherein a perfusate flows continuously from the organ-on-a-chip to the detection unit during the quantitating of the amount of insulin.

20. An interface device for use in fluidic transfer, the device comprising:
a cap for a reservoir, wherein the cap defines a first opening and a second opening, wherein said first opening and said second opening are disposed at distinct locations of the cap;
a capillary tube disposed in the first opening of the cap; and
an electrode disposed in the second opening of the cap, wherein the electrode has a first terminus that is positioned in the reservoir,
wherein the device is configured to provide an interface between two apparatuses.

* * * * *